United States Patent [19]

Stephen et al.

[11] Patent Number: 4,559,033

[45] Date of Patent: * Dec. 17, 1985

[54] APPARATUS AND METHODS FOR MINIMIZING PERITONEAL INJECTION CATHETER OBSTRUCTION

[75] Inventors: Robert L. Stephen; Carl Kablitz; Barry K. Hanover; Stephen C. Jacobsen; Jeffrey J. Harrow, all of Salt Lake City, Utah

[73] Assignee: University of Utah Research Foundation, Salt Lake City, Utah

[ * ] Notice: The portion of the term of this patent subsequent to Aug. 23, 2000 has been disclaimed.

[21] Appl. No.: 522,907

[22] Filed: Aug. 12, 1983

Related U.S. Application Data

[63] Continuation-in-part of Ser. No. 200,830, Oct. 27, 1980, Pat. No. 4,400,169, which is a continuation-in-part of Ser. No. 235,185, Feb. 17, 1981, Pat. No. 4,405,305.

[51] Int. Cl.$^4$ .................. A61M 5/00; A61M 31/00
[52] U.S. Cl. ........................................... 604/49; 604/48; 604/51; 604/93; 604/174; 604/185; 604/265; 604/266; 604/267
[58] Field of Search ........................ 604/8–10, 604/29, 49, 48, 50, 51, 73, 93, 117, 132, 174, 175, 181, 185, 246, 891, 265.6, 267; 128/1 R

[56] References Cited

U.S. PATENT DOCUMENTS

| | | | |
|---|---|---|---|
| 3,137,299 | 6/1964 | Tabor | 128/351 |
| 3,310,051 | 3/1967 | Schulte | 128/216 |
| 3,396,727 | 8/1968 | Mount | 128/349 |
| 3,580,983 | 5/1971 | Jackson | 174/47 |
| 3,633,585 | 1/1972 | McDonald, Jr. | 128/348 |
| 3,703,899 | 11/1972 | Calinog | 604/267 |
| 3,783,868 | 1/1974 | Bokros | 128/260 |
| 3,818,511 | 6/1974 | Goldberg et al. | 3/1 |
| 4,054,139 | 10/1977 | Crossley | 128/260 |

(List continued on next page.)

FOREIGN PATENT DOCUMENTS

2072514 3/1981 United Kingdom .
2073024 8/1981 United Kingdom .

OTHER PUBLICATIONS

Merrill et al., "The Use of an Inlying Plastic Conduit for Chronic Peritoneal Irrigation", *Trans. Amer. Artif. Inter. Organs*, 8:252–255 (1962).

Boen et al., "Periodic Peritoneal Dialysis in the Management of Chronic Uremia", *Trans. Amer. Soc. Artif. Inter. Organs*, 8:256–262 (1962).

(List continued on next page.)

*Primary Examiner*—C. Fred Rosenbaum
*Assistant Examiner*—Mario Costantino
*Attorney, Agent, or Firm*—Workman, Nydegger & Jensen

[57] ABSTRACT

The present invention is directed to subcutaneous peritoneal injection catheters and methods which minimize catheter obstruction during use. The apparatus includes a receiving chamber or reservoir having a relatively small internal volume while employing a penetrable membrane and relatively enlarged target surface area. The reservoir is interconnected with the peritoneal cavity by a hollow stem. The penetrable membrane accommodates a hollow needle being inserted into the receiving reservoir and is configured with a dome-like profile so that the membrane may also be depressed to expel insulin from the receiving reservoir into the peritoneal cavity in a direction generally toward the mesenteric peritoneal membrane.

The distal end of the hollow stem (which is situated inside the peritoneal cavity), is constructed so as to minimize the likelihood of catheter obstruction during use by a patient. For example, in one presently preferred embodiment of the invention, the distal end of the stem is provided with two, parallel, diametrally enlarged flanges. The two flanges are unequal in size, and they are positioned on the stem such that the larger flange resides against the peritoneal membrane and the smaller flange is located immediately adjacent the distal opening of the stem. In addition, an antibacterial agent may be placed within the device, and the device may also be formed of or coated with a substance which inhibits body cell and bacterial growth.

56 Claims, 8 Drawing Figures

U.S. PATENT DOCUMENTS

| | | | |
|---|---|---|---|
| 4,160,454 | 7/1979 | Foux | 128/348 |
| 4,184,497 | 1/1980 | Kolff et al. | 131/213 |
| 4,253,463 | 3/1981 | Kim | 128/348 |
| 4,256,102 | 3/1981 | Monaco | 128/213 |
| 4,368,737 | 1/1983 | Ash | 604/175 |
| 4,400,169 | 8/1983 | Stephen | 604/49 |
| 4,405,305 | 9/1983 | Stephens et al. | 604/49 |
| 4,490,137 | 12/1984 | Moukheibir | 604/28 |

OTHER PUBLICATIONS

Barry et al., "A New Flexible Cannula and Seal to Provide Prolonged Access to the Peritoneal Cavity for Dialysis", *Trans. Amer. Soc. Artif. Inter. Organs*, 9:105–107 (1963).

Henderson et al., "Further Experience with the Inlying Plastic Conduit for Chronic Peritoneal Dialysis", *Trans. Amer. Soc. Artif. Inter. Organs*, 9:108–116 (1963).

Palmer et al., "Prolonged Peritoneal Dialysis for Chronic Renal Failure", *The Lancet*, 1:700–702 (1964).

Malette et al., "A Clinically Successful Subcutaneous Peritoneal Access Button for Repeated Peritoneal Dialysis", *Trans. Amer. Soc. Artif. Organs*, 10:396–398 (1964).

Moyer et al., "Treatment of Large Human Burns With 0.5% Silver Nitrate Solution", *Archives of Surgery*, 90:812–867 (Jun. 1965).

Jacob et al., "Repeated Peritoneal Dialysis by the Catheter Replacement Method: Description of Technique and a Replaceable Prosthesis for Chronic Access to the Peritoneal Cavity", *Proc. EDTA* (1967), pp. 136–140.

Fox, Jr., "Silver Sulfadiazine—A New Topical Therapy for Pseudomonas in Burns", *Archives of Surgery*, 96:184–188 (Feb. 1968).

Tenckhoff et al., "A Bacteriologically Safe Peritoneal Access Device", *Trans. Amer. Soc. Artif. Inter. Organs*, 14:181–186 (1968).

Brewer et al., "Indwelling Peritoneal (Tenckhoff) Dialysis Catheter", *JAMA*, vol. 219, No. 8, pp. 1011–1015 (Feb. 21, 1972).

Modak et al., "Binding of Silver Sulfadiazine to the Cellular Components of Pseudomonas Aeruginosa", *Biochemical Pharmacology*, 22:2391–2404 (Great Britain, 1973).

Fox, Jr. et al., "Mechanism of Silver Sulfadiazine Action on Burn Wound Infections", *Antimicrobial Agents and Chemotherapy*, 5:582–588 (U.S.A.; Jun., 1974).

Felig, "Insulin: Rates and Routes of Delivery", *New England Journal of Medicine*, 291:103–104 (U.S.A. 1974).

Karanicolas et al., "Home Peritoneal Dialysis: 3 Years' Experience in Toronto", *CMA Journal*, 116:266–269 (Canada, Feb. 5, 1977).

Fox, Jr. et al., "Topical Chemotherapy for Burns Using Cerium Salts and Silver Sulfadiazine", *Surgery, Gynecology & Obstetrics*, 144:668–672 (May, 1977).

Oreopoulos, "Renewed Interest in Chronic Peritoneal Dialysis", *Kidney International*, vol. 13, Supp. 8, pp. S-117 to S-119 (1978).

Nolph, "Effects of Intraperitoneal Vasodilators on Peritoneal Clearances", *Proceedings 11th Ann. Contractors' Conference* (1978), pp. 29–33.

Ash et al., "The Column Disc Peritoneal Catheter: A Peritoneal Access Device with Improved Drainage", *ASAIO Journal*, 3:109–115 (Jul./Sep., 1980).

Schade et al., "Normalization of Plasma Insulin Profiles with Intraperitoneal Insulin Infusion in Diabetic Man", *Diabetologia*, 19:35–39 (1980).

Kablitz et al., "Subcutaneous Peritoneal Access Device Used for Intraperitoneal Insulin Treatment of Non-Uraemic Diabetic Patients", *Proceedings of the Second International Symposium on Peritoneal Dialysis* (1981), pp. 170–172.

Stephen et al., "Long-Term Intraperitoneal Insulin Treatment: Preliminary Studies in 12 Diabetic Patients", *Diabetic Renal-Retinal Syndrome*, 2:447–461 (1982).

Stephen et al., "Stabilization and Improvement of Renal Function in Diabetic Nephropathy", *Diabetic Nephropathy*, 1:8–13 (1982).

Felig, *Diabetes Its Physiological and Biochemical Basis*, pp. 100–103 (U.S.A., 1980).

APPARATUS AND METHODS FOR MINIMIZING PERITONEAL INJECTION CATHETER OBSTRUCTION

RELATED APPLICATIONS

This application is a continuation-in-part application of our copending application Ser. No. 200,830 filed Oct. 27, 1980 for SUBCUTANEOUS PERITONEAL INJECTION CATHETER, which issued as U.S. Pat. No. 4,400,169 on Aug. 23, 1983. This application is also a continuation-in-part application of our copending application Ser. No. 235,185 filed Feb. 17, 1981 for SUBCUTANEOUS PERITONEAL INJECTION CATHETER, which issued as U.S. Pat. No. 4,405,305 on Sept. 20, 1983 and which is a continuation-in-part application of our copending application Ser. No. 200,830 filed Oct. 27, 1980 for SUBCUTANEOUS PERITONEAL INJECTION CATHETER.

BACKGROUND

1. The Field of the Invention

This invention relates to implantable peritoneal injection catheters and, more particularly, to novel apparatus and methods for minimizing obstruction of subcutaneous peritoneal injection catheters during the period of implantation.

2. The Prior Art

A large proportion of the various chemical reactions that occur in the body are concerned with making energy in foods available to the various physiological systems in the cells. Metabolism of glucose is particularly important in many of these chemical reactions, and the body has a very sophisticated regulatory system adapted to maintain blood glucose levels at an optimum level so that adequate amounts of glucose will be available as needed.

One of the most important elements in the glucose regulatory system is the hormone "insulin." Insulin is a relatively small protein, having a molecular weight of only 5743 daltons; it is comprised of two amino acid chains connected by a pair of disulfide linkages.

Insulin has the ability to regulate glucose metabolism in two ways. First, insulin has the ability to increase the rate of glucose transport through the cell membrane of many types of cells in the body. In the absence of insulin, the rate of glucose transport into these cells is reduced to less than one-fourth of the normal rate. On the other hand, excessive levels of insulin can increase the rate of glucose transport to nearly five times normal. Adjustments in the level of insulin in the body can thus be seen to have the capability of adjusting the rate of glucose absorption by twentyfold.

In addition to its role in glucose transport, insulin also acts as a regulatory hormone. Normally, when digestion results in rising levels of glucose in the body, certain cells in the pancreas, known as "beta cells" of the "islets of Langerhans," commence secreting insulin into the portal vein. About half of the secreted insulin is immediately absorbed by the liver, with the remaining portion being distributed through most of the rest of the body.

In response to the rising level of insulin, the liver produces large quantities of an enzyme known as glucokinase which causes conversion of glucose into glycogen which is then stored. Importantly, a large portion of the excess glucose entering the blood system as a product of digestion is rapidly removed by the liver in order to maintain relatively normal concentrations of glucose in the bloodstream.

Later, when the blood glucose level begins to drop below normal, the pancreas reduces its secretion of insulin, and the "alpha cells" of the islets of Langerhans commence secretion of a hormone known as "glucagon." Glucagon stimulates the conversion of glycogen in the liver into glucose by activating another enzyme known as liver phosphorylase. This, in turn, results in release of glucose into the bloodstream for transport throughout the body.

From the foregoing, it will be appreciated that the pancreas and the liver play a major role in regulating the level of glucose in the bloodstream. Unfortunately, the delicate balance between the actions of the pancreas and the liver can be easily upset. For example, it is not uncommon for the pancreas to suffer damage so that it no longer secretes adequate levels of insulin. This condition is known as "diabetes mellitus," or more commonly, simply "diabetes." Serious cases of diabetes often exhibit a total cessation of insulin secretion.

As would be expected, insufficient secretion of insulin substantially reduces the transport of glucose into most tissues of the body. (The most notable exception is the brain; glucose transport across the blood-brain barrier is dependent upon diffusion rather than insulin-mediated transport.) Further, the glucose regulatory function is also impaired since, in the absence of insulin, little glucose is stored in the liver during times of excess and, hence, is not available for subsequent release in times of glucose need.

One result of the lack of sufficient quantities of insulin in the body is a rise in the blood glucose concentration. This causes the osmotic pressure in extracellular fluids to rise above normal, which in turn often results in significant cellular dehydration. This problem is exacerbated by the action of the kidneys which act to remove excessive quantities of glucose from the blood; the increase in glucose concentration in the kidneys causes yet additional fluids to be removed from the body. Thus, one of the significant effects of diabetes is the tendency for dehydration to develop.

However, an even more serious effect occurs because of the failure of body tissues to receive adequate levels of glucose. In the absence of adequate levels of glucose, the metabolism of body cells switches from carbohydrate metabolism to fat metabolism. When the body is required to depend heavily upon fat metabolism for its energy, the concentration of acetoacetic acid and other keto acids rises to as much as thirty times normal, thus causing a reduction in the pH of the blood below its normal pH level of 7.4.

Again, this problem is exacerbated by the kidneys. As the kidneys remove the various keto acids from the blood, substantial amounts of sodium are also lost, thereby resulting in even further decreases in blood pH. If the blood pH is reduced to below about 7.0, the diabetic person will enter a state of coma; and this condition is usually fatal.

The generally accepted treatment for diabetes is to administer enough insulin so as to restore carbohydrate metabolism. Traditionally, administration of insulin has been by injections into the peripheral circulation, either from an intramuscular or subcutaneous injection. Although widely used, this form of treatment has several disadvantages.

First, using peripheral insulin administration, only about ten percent of the administered insulin reaches the liver, as compared to approximately fifty percent in normal persons. As a consequence, hepatic glucose production is not reduced first; rather, blood glucose is lowered due to the presence of high levels of insulin in the peripheral circulation by increased utilization of the blood glucose by other tissues (such as muscle and fat). Hence, normal levels of blood sugar are achieved only by carefully matching any increased peripheral utilization of blood sugar to an increased hepatic production. This is inherently much more difficult than simply decreasing hepatic glucose production.

Additionally, these traditional administration methods fail to provide the type of control over the blood glucose concentration that occurs in a normal person. Clearly, once- or twice-daily injections of insulin cannot supply controlled variable amounts of insulin in response to changing metabolic demands during the course of the day. Hence, when using traditional insulin administration methods, the blood glucose content tends to fluctuate between normally high and low concentrations. Significantly, there are some indications that such periodic rise and fall of glucose concentrations between hyperglycemia and hypoglycemia contributes to devastating vascular and neurological complications over a period of time. (It is not uncommon, for example, for a long-term diabetic to experience atherosclerosis, arteriosclerosis, hypertension, severe coronary heat disease, retinopathy, cataracts, chronic renal disease, or loss of circulation in the extremities.)

Another consequence of massive injections of insulin on a periodic basis is that excessive amounts of insulin occasionally enter the bloodstream, thereby causing glucose to be rapidly transported into the cells and decreasing the blood glucose to substantially below normal levels. Unfortunately, diabetic patients already have little glucose reserve, since the liver, in its state of under-insulinization, is already releasing glucose. Consequently, the blood sugar level will plummet despite adequate levels of counterregulatory hormones (such as glucagon, epineephrine, norepinephrine, and growth hormones), which normally would increase liver production of glucose in emergency situations.

Importantly, if the blood glucose level is reduced too much, there will be insufficient glucose to diffuse across the blood-brain barrier, and the brain and central nervous system will begin to suffer from depressed metabolism. This hypoglycemic reaction (having a progression of symptoms from nervousness, sweating, stupor, and unconsciousness to occasionally irreparable brain damage), will occur until sugary substances are taken either by mouth or intravenously.

The resulting ongoing cycle between hyperglycemia and hypoglycemia has created a basic rift in the philosophy of diabetic control. The "tight control" philosophy claims that the long-term devastations of diabetes (that is, blindness, heart attacks, kidney failure, and loss of extremities), are due to abnormally elevated sugar levels. Those ascribing to this "tight control" philosophy strive to keep blood sugar within the normal range even at the risk of frequent (more than once a week) hypoglycemic reactions. The converse "loose control" philosophy is based upon the presumption that the basic premise of the "tight control" philosophy has yet to be proved and that the considerable risks of hypoglycemic reactions are not worth an unproved benefit.

In an effort to avoid the undesirable effects of the traditional insulin administration methods, various closed and open loop control delivery systems have been developed. Closed loop delivery systems are synonymous with prolonged hospitalization. Additionally, they are awkward to wear, they require tubing sets and implanted needles and, in spite of claims made to the contrary, they can malfunction ("surge"), usually at the most inconvenient hours.

Open loop delivery systems, on the other hand, actually produce a more sustained, if somewhat better regulated, hyperinsulinemic state. The therapists involved persist in using both open and closed loop systems to deliver insulin peripherally, thereby giving rise to many of the difficulties already mentioned.

Consequently, due to the problems and difficulties set forth above, those skilled in the art of treating diabetes have sought to find improved methods for administering therapeutic insulin to diabetic individuals. Perhaps one of the most promising insulin administration methods which is currently being investigated comprises the administration of insulin via the peritoneum.

The peritoneum is the largest serous membrane in the body and consists (in the male) of a closed sac, a part of which is applied against the abdominal parietes, while the remainder is reflected over the contained viscera. (In the female, the peritoneum is not a closed sac, since the free ends of the uterine and fallopian tubes open directly into the peritoneal cavity.)

The part of the peritoneum which lines the abdominal wall is named the parietal peritoneum and that which is reflected over the contained viscera constitutes the mesenteric (visceral) peritoneum. The space between the parietal and mesenteric layers of the peritoneum is called the peritoneal cavity. However, under normal conditions, this "cavity" is merely a potential one, since the parietal and mesenteric layers are typically in contact.

Of particular significance, a portion of the blood circulation of the peritoneum leads directly into the portal venous system. Hence, any insulin absorbed by the peritoneum would potentially have nearly direct access to the liver. As a result, such insulin would first be available to reduce hepatic glucose production, and the insulin could, therefore, potentially function more effectively in its glucose regulatory capacity.

For a number of years, it has been well-known that the peritoneal membrane will function fairly effectively as an exchange membrane for various substances. Thus, as early as 1923, peritoneal dialysis was first applied clinically. At the present time, peritoneal dialysis is being used with increasing frequency to treat individuals suffering from end-stage renal disease.

In a typical peritoneal dialysis treatment, approximately two liters of dialysate is infused into the peritoneal cavity. Then, after the dialysate has remained within the peritoneal cavity for a period of time, thereby permitting the necessary diffusion across the peritoneal membrane, the dialysate is removed. This procedure is typically repeated a number of times during each dialysis treatment. Thus, in simple terms, the peritoneal cavity, together with the dialysate, functions as an artificial kidney.

The performance of peritoneal dialysis necessarily requires some type of peritoneal access device. The first peritoneal access device was a piece of rubber tubing temporarily sutured in place. By 1960, peritoneal dialysis was becoming an established form of artificial kidney therapy; and, in order to lessen the discomfort of repeated, temporary punctures into the peritoneal cavity, various access devices permitting the painless insertion of acute or temporary peritoneal catheters were developed.

The most common peritoneal access device is of the Tenckhoff type in which a capped, percutaneous, silastic tube passes through the abdominal wall into the peritoneal cavity. Another peritoneal access device (the "Gottloib" prosthesis) consists of a short, "gold tee" shaped device which is adapted to be placed under the skin with a hollow tubular portion extending just into the peritoneal cavity. This cavity is designed specifically to allow the insertion of an acute peritoneal catheter (or trocar) through the skin and down through this access tubing directly into the peritoneal cavity.

Another device consists of a catheter buried underneath the skin and extending into the peritoneal cavity via a long tubing. Peritoneal dialysis is performed by inserting a large needle into the subcutaneous portion of the catheter.

When using such access devices, a variety of drugs or other fluids have sometimes been added to the large volumes of peritoneal dialysis solutions and thereby installed into the peritoneal cavity for various therapeutic reasons. Some examples of these drugs are antibiotics, amino acids, and insulin. However, such therapeutic maneuvers are merely fortuitous, in that the clinician is simply taking advantage of a particular situation, that is, a peritoneal access device implanted in a particular group of patients. Importantly, there are cogent reasons for not using existing, permanent peritoneal access devices for simple drug injections in a wide variety of patients not suffering from end-stage renal disease.

First, the majority of prior art peritoneal access devices are long, clumsy, percutaneous, infection-prone silastic tubes. Hence, it is undesirable that any patient would wear such a device on a permanent or semi-permanent basis, unless it is absolutely necessary.

In addition, most of the prior art peritoneal access devices have a relatively large internal volume, that is, relatively large volumes of fluid are required in order to fill the devices. As mentioned above, during a typical dialysis treatment, approximately two liters of dialyzing fluid is injected into the peritoneal cavity at one time. Thus, when existing devices are used for purposes of peritoneal dialysis, the relatively large internal volume of the device is of little consequence. However, when injecting small quantities of fluid or drugs into the peritoneal cavity, this volume is a very real hindrance since the injected fluid may simply remain within the device itself instead of entering the peritoneal cavity.

Further, it has been found that bacteria will sometimes accumulate and grow within the prior art access devices. Also, the prior art peritoneal access devices often become obstructed by body cells and/or bacterial after they are implanted in a patient. In many cases, such obstruction cannot be eliminated without damaging the device, and the access device must, therefore, be removed.

Accordingly, it would be an improvement in the art to provide a peritoneal catheter apparatus which can be used to inject small volumes of fluid into the peritoneal cavity and which would minimize the opportunity for catheter obstruction. It would also be an improvement in the art to provide a peritoneal injection catheter apparatus and method which minimizes the accumulation or growth of body cells on the catheter. In addition, it would be an improvement in the art to provide an apparatus and method for minimizing the occurrence of bacterial growth on or in a peritoneal injection catheter. Further, it would be an improvement in the art to provide an apparatus and method for minimizing the occurrence of peritoneal injection catheter obstruction which would preserve the structural integrity of the catheter. Such devices and methods are disclosed and claimed herein.

BRIEF SUMMARY AND OBJECTS OF THE INVENTION

The present invention relates to a novel subcutaneous peritoneal injection catheter apparatus and methods which minimize catheter obstruction during use.

The apparatus includes a receiving chamber or reservoir having a relatively small internal volume while employing a penetrable membrane and relatively enlarged target surface area. The reservoir is interconnected with the peritoneal cavity by a hollow stem. The penetrable membrane accommodates a hollow needle being inserted into the receiving reservoir and is configurated with a dome-like profile so that the membrane may also be depressed to expel insulin from the receiving reservoir into the peritoneal cavity in a direction generally toward the mesenteric peritoneal membrane.

The distal end of the hollow stem (which is situated inside the peritoneal cavity), is constructed so as to minimize the likelihood of catheter obstruction during use by a patient. For example, in one presently preferred embodiment of the invention, the distal end of the stem is provided with two, parallel, diametrally enlarged flanges. The two flanges are unequal in size, and they are positioned on the stem such that the larger flange resides against the peritoneal membrane and the smaller flange is located immediately adjacent the distal opening of the stem. In addition, an antibacterial agent may be placed within the device, and the device may also be formed of or coated with a substance which inhibits body cell and bacterial growth.

It is, therefore, a primary object of this invention to provide an improved implantable peritoneal injection catheter which minimizes the possibility of catheter obstruction due to cell ingrowth and/or overgrowth.

It is also an object of the present invention to provide an improved, subcutaneously implantable peritoneal injection catheter which minimizes the likelihood of bacterial growth within the subcutaneous reservoir of the catheter.

It is a further object of this invention to provide a method for minimizing or eliminating peritoneal injection catheter obstruction which will maintain the structural integrity of the peritoneal catheter.

Finally, it is an object of this invention to provide an improved implantable subcutaneous peritoneal injection catheter which may be used by a single patient over a relatively long period of time without interruption or malfunction.

These and other objects and features of the present invention will become more fully apparent from the following description and appended claims taken in conjunction with the accompanying drawings.

DETAILED DESCRIPTION OF THE PREFERRED EMBODIMENTS

Figure 1:
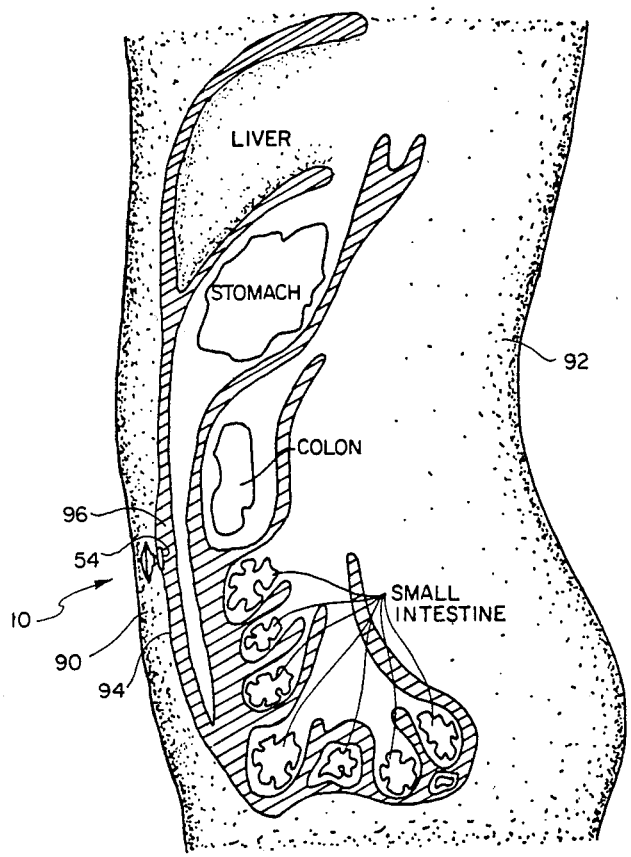
FIG. 1 is a schematic illustration of a subcutaneous peritoneal injection catheter shown implanted in the abdominal wall of a torso.

This invention comprises an improvement to the subcutaneous peritoneal injection catheters disclosed in our copending applications: Ser. No. 235,185 filed Feb. 17, 1981, and Ser. No. 200,830 filed Oct. 27, 1980.

GENERAL DISCUSSION

As an alternative to both intravenous and intramuscular insulin delivery, portal venous administration of insulin has given highly encouraging results in experimental animals: less insulin is required to achieve normoglycemia and hyperinsulinemia is avoided. Long-term access directly into the portal system, however, carries several severe risks, all of which are lethal. Nevertheless, there is a secondary and much safer route leading directly into the portal venous system—the mesenteric (visceral) peritoneal membrane. Although access to the intraperitoneal site is more difficult, it has the potential advantages of avoiding peripheral hyperinsulinemia, insulinizing the liver via direct portal venous system insulin absorption, and more rapid absorption than subcutaneously delivered insulin.

As alluded to above, when administering insulin via the peritoneum, it is most desirable that the insulin be substantially absorbed by the mesenteric, rather than the parietal, peritoneal membrane. If the insulin is absorbed by the parietal peritoneal membrane, the insulin enters the body's general systemic venous system. The effect is thus the same as if the insulin had been injected intramuscularly; that is, the insulin is gradually absorbed into the peripheral circulatory system and only a portion of the insulin reaches the liver. As a result, control of glycemia is not significantly better than that achieved by conventional intramuscular injections. If the injected insulin is absorbed by the mesenteric peritoneal membrane, on the other hand, the insulin is absorbed into the portal venous system and made readily available to the liver.

Preliminary results of experiments using intraperitoneal delivery of insulin appear favorable. Insulin delivery into the peritoneum is reported to have resulted in a rapid rise in circulating peripheral insulin concentration, which peaked at 30–45 minutes following the initiation of insulin delivery. Furthermore, when the infusion rate of intraperitoneal insulin was reduced to the background rate, a gradual decline in peripheral insulin concentration to normal fasting values resulted. (This free insulin response is a marked contrast to the continuing high levels following intramuscular insulin injection.)

It was, therefore, concluded that normalization of plasma insulin profiles was achievable with intraperitoneal infusion of insulin and, further, that meal-related hyperglycemia (elevated blood glucose) is well-controlled with intraperitoneal insulin, yet hypoglycemic episodes are reduced compared to subcutaneous delivery. See, D. S. Schade, R. P. Eaton, N. M. Friedman, & W. J. Spencer, "Normalization of Plasma Insulin Profiles With Intraperitoneal Insulin Infusion in Diabetic Man," 19 DIABETOLOGIA 35–39 (1980).

Intraperitoneal delivery of insulin has been performed in ketosis-prone diabetic human subjects on a short-term basis (i.e., a matter of hours). Such intraperitoneal delivery achieves comparable glycemic control to that achieved with intramuscular insulin, with only approximately half the integrated blood levels of plasma insulin. Intraperitoneal insulin has also been utilized long term in patients with ketosis-prone diabetes and end-stage renal disease who were being treated by continuous ambulatory peritoneal dialysis. Adequate control was achieved in the three patients reported.

There appears to be no conclusive documentation substantiating the thesis that the intraperitoneal delivery of drugs is primarily absorbed into the portal venous system (mesenteric peritoneum) rather than the general systemic venous system (parietal peritoneum). However, there is a considerable amount of indirect evidence for this hypothesis: (1) in laparatomy one's field of vision is virtually totally obscured by the mesenteric peritoneum; (2) the work of other researchers indicates that control of glycemia by intraperitoneal insulin administration is good, even though there was a 50% "loss" of insulin—presumably picked up by the liver before reaching the peripheral circulation; and (3) intraperitoneal administration of sodium nitroprusside (for the purpose of causing intraperitoneal vaso-dilation) results in no detectable levels of peripheral plasma thiocyanate. (It is assumed that metabolism of nitroprusside by the liver accounted for the lack of peripheral thiocyanate.)

In our copending patent applications Ser. No. 235,185 filed Feb. 17, 1981 and Ser. No. 200,830 filed Oct. 27, 1980 for SUBCUTANEOUS PERITONEAL INJECTION CATHETER, we disclose a peritoneal injection catheter having, inter alia, the following features: (1) the internal volume of the device is minimal; (2) it presents a large surface area (consistent with the first constraint) to allow for injection of various drugs; (3) it is designed purely and simply for one-way flow, i.e., drug injection is inward only; (4) it is designed so that a variety of drugs may be injected into the peritoneal cavity toward the mesenteric peritoneal membrane; (5) it has a resilient, dome-shaped surface above the receiving reservoir so that the dome may be depressed to expel insulin from the receiving reservoir into the peritoneal cavity; and (6) it is not designed for peritoneal dialysis and, in fact, would not function if used for this purpose. This peritoneal injection catheter has been quite successful for use in administering insulin to diabetic patients. However, in spite of this success, some difficulties have been observed.

First, it has been noted that this catheter occasionally becomes obstructed after it is implanted in a patient. At present, the chief causes of such catheter obstruction appear to be the accumulation of body cells in the peritoneal opening, tissue growth over or within the peritoneal opening, and total or partial occlusion by the greater omentum. Such obstruction, of course, interrupts catheter use, and the obstruction may be difficult to remove. Additionally, when attempting to dislodge the obstruction from the peritoneal catheter, the peritoneal catheter may occasionally rupture, thereby necessitating complete removal of the catheter.

Second, it has also been noted that bacterial growth may occur with the catheter. When using the subcutaneous peritoneal injection catheter, the patient injects insulin into the device, and the fluid thereafter disperses into the peritoneal cavity. Until recently it has been assumed, probably correctly, that any bacteria driven through the skin by the needle and then transported into the peritoneal cavity would probably cause very little harm. The basis of this assumption is that the peritoneal cavity has some very effective defense mechanisms against invading microorganisms and the number that could be forced into the cavity with the head of a 25 g needle (0.51 mm in diameter) would not represent an overwhelming invasion.

Unfortunately, however, the small subcutaneous reservoir inherent in the device itself is not so protected. The omentum in the peritoneal cavity cannot reach into this region, and mesenteric lymph glands are remote. Thus, the only possible means of combating microorganisms that may be residing in the reservoir would be with microbiocidal chemicals and the few white cells which free peritoneal fluid contains.

THE PREFERRED EMBODIMENTS

The peritoneal catheter of the present invention is constructed so as to minimize both obstruction of the peritoneal catheter and the growth of bacteria within the peritoneal catheter during use by a patient. The invention is best understood by reference to the drawings wherein like parts are designated with like numerals throughout.

Referring now more particularly to FIG. 1, peritoneal catheter 10 is shown implanted in the abdominal wall 90 of a torso 92 and provides fluid communication with peritoneal catheter 10 with the peritoneal membrane 94 surrounding peritoneal cavity 96. It should be noted that peritoneal cavity 96 is shown somewhat distended as though infused with dialysate, in order to more clearly set forth the environment of peritoneal catheter 10.

After peritoneal catheter 10 is implanted and use has commenced, the distal end 54 of peritoneal catheter 10 occasionally becomes obstructed. Such obstruction may be due to the ingrowth and/or the accumulation of body cells in peritoneal catheter 10.

Similarly, peritoneal catheter 10 may sometimes become obstructed by an overgrowth of a portion of peritoneal membrane 94, called the omentum. Also, the obstruction may arise due to the uninhibited growth of bacterial cells within peritoneal catheter 10. The present invention comprises several alternative configurations of and/or attachments to peritoneal catheter 10 which serve to minimize the probability of such catheter obstruction and bacterial growth.

Figure 2:
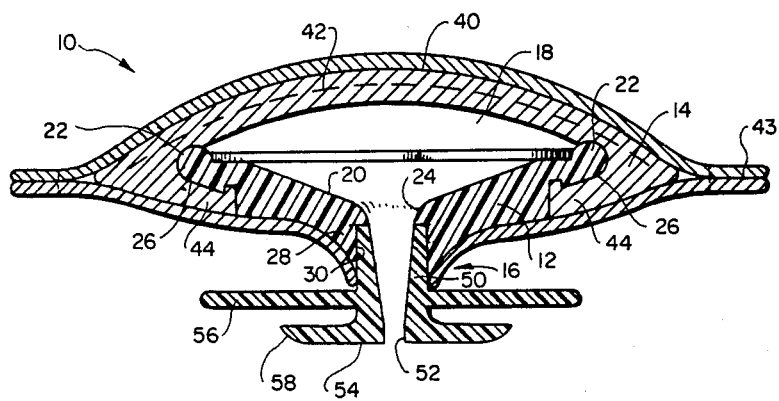
FIG. 2 is a vertical cross-sectional view of one presently preferred embodiment of the present invention.
Figure 3:
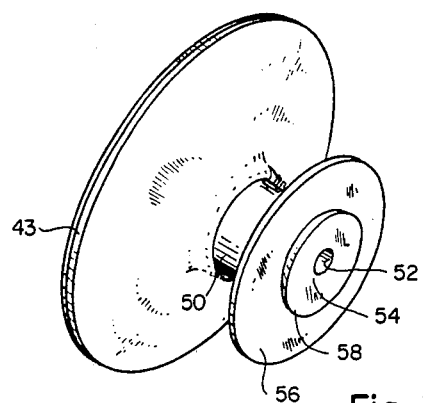
FIG. 3 is a bottom perspective view of the embodiment depicted in FIG. 2.

Referring now more particularly to FIGS. 2 and 3, one presently preferred embodiment of the peritoneal catheter apparatus of this invention, designated generally as 10, includes a body 12, a cap 14, and a stem 16. Body 12 serves as the basal member for peritoneal catheter 10 and is configured with a funnel-like section 20 having a relatively shallow depth in comparison with the relatively enlarged diameter. The depth of funnel section 20 is selectively predetermined so as to contain a body of insulin which may be suitable retained momentarily or expelled, as desired.

Funnel section 20 is surrounded at its upper edge by an upstanding rim 22 and terminates downwardly toward its center in a throat 24. Body 12 is fabricated from a suitable, puncture resistant plastic material such as, for example, a conventional, biocompatible polyurethane. Body 12 is also provided with sufficient thickness so as to preclude inadvertent puncture by a needle.

The opposite edge of rim 22 is formed as a retainer shelf 26 for the purpose of retaining an edge or lip 44 of cap 14. The lower portion of body 12 includes a neck 28 having a coaxial counterbore 30. The internal diameter of counterbore 30 is selectively predetermined so that column 50 may be telescopically received into abutment with throat 24, as will be set forth more fully below.

Cap 14 is configured with an outwardly curved dome-like puncture zone shown as dome 40. The outer circumference of cap 14 includes an inwardly directed circumferential lip 44 adapted to be received in snap-fit relationship with shelf 26 for the purpose of mounting cap 14 to body 12. The height of rim 22, as well as the diameter and the depth of funnel section 20 in combination with the hemispherical radius of cap 14, selectively predetermine the volume of the resulting receiving reservoir 18.

Cap 14 is fabricated from a suitable biocompatible material (such as silicone rubber) having the desired characteristics of being: (a) resilient, (b) readily penetrable, and (c) resealable to accommodate being flexed and punctured numerous times without degradation of the structural integrity of cap 14. A reinforcing material 42 is preferably imbedded in the biocompatible material of cap 14. Also, a portion of cap 14 and body 12 may be covered with a suitable, biocompatible velour material 43 to accommodate tissue ingrowth.

Stem 16 is configured as a hollow tubular column 50 having a hollow lumen 52 extending therethrough. As previously mentioned, stem 16 is telescopically received into abutment with throat 24. The diameter of lumen 52 matches the diameter of throat 24 so as to provide a continuous, smooth flow channel through peritoneal catheter 10.

The distal end 54 of tubular column 50 is provided with two, diametrally enlarged flanges 56 and 58. As shown, flange 58 is somewhat smaller than flange 56 and is located immediately adjacent to distal end 54 of tubular column 50. Advantageously, the outer edges of flange 58 are somewhat rounded, as shown, such that flange 58 has no sharp edges which could injure adajcent tissue.

Tubular column 50, together with flanges 56 and 58, may be formed as a single unit, as shown. Alternatively, tubular column 50 and flange 56 may be formed as a single unit, with flange 58 being attached to a smaller tubular column which is adapted to be snugly received within lumen 52.

In use, peritoneal catheter 10 is fist surgically implanted in a patient. This is accomplished by making an incision in the patient's abdominal wall 90 and peritoneal membrane 94 (see FIG. 1). The peritoneal catheter is then placed in the patient such that distal end 54 of stem 16 extends into peritoneal cavity 96 with flange 56 being against peritoneal membrane 94. Peritoneal catheter 10 is then secured in place by means of sutures.

Once peritoneal catheter 10 is in place, the user injects insulin into receiving reservoir 18 by penetrating dome 40 with a conventional, hollow needle. Advantageously, the insulin in receiving reservoir 18 may be allowed to slowly percolate through lumen 52 into peritoneal cavity 96 or, upon demand, the user may depress dome 40 with a finger to forceably expel insulin from receiving reservoir 18 through lumen 52 into peritoneal cavity 96.

In the event that body tissue or cells should begin to grow or accumulate adjacent flange 56 of peritoneal catheter 10, the cells would grow along the surfac of flange 56 so as to grow into the space between flange 56 and flange 58. Thereafter, the tissue would be forced to double back on itself in order to continue its growth. It is well known that, unless the growth is cancerous, cell growth will cease as soon as the tissue doubles back on itself. In any event, it is highly unlikely that the cells would thereafter grow outward and upward over the top of flange 58, thereby occluding the distal end 54 of tubular column 50.

Experimental catheters having substantially the same configuration as the catheter depicted in FIGS. 2 and 3 have been implanted in six diabetic patients to date. Each of these catheters has remained free from any obstruction during the period of implantation (approximately six months). Significantly, when two of these catheters were subsequently removed (due to unrelated, accidental, traumatic injuries to the patient's abdominal area), it was noted that body tissue had, in fact, grown over flange 56 of the catheters. However, such overgrowth had stopped once the tissue reached column 50, and no tissue growth over flange 58 had occurred.

Figure 4:
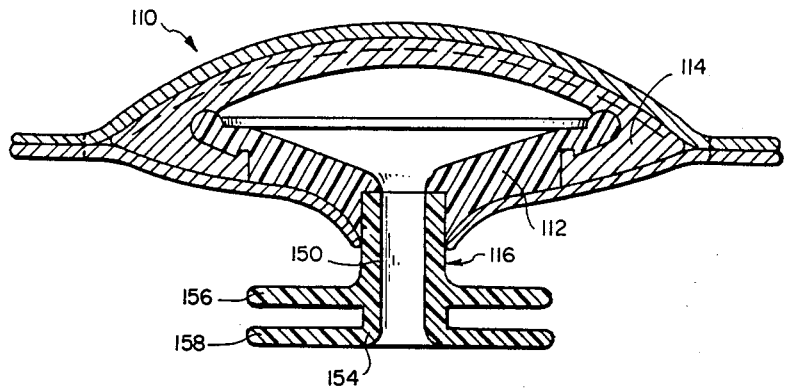
FIG. 4 is a vertical cross-sectional view of a second preferred embodiment of the present invention.
Figure 5:
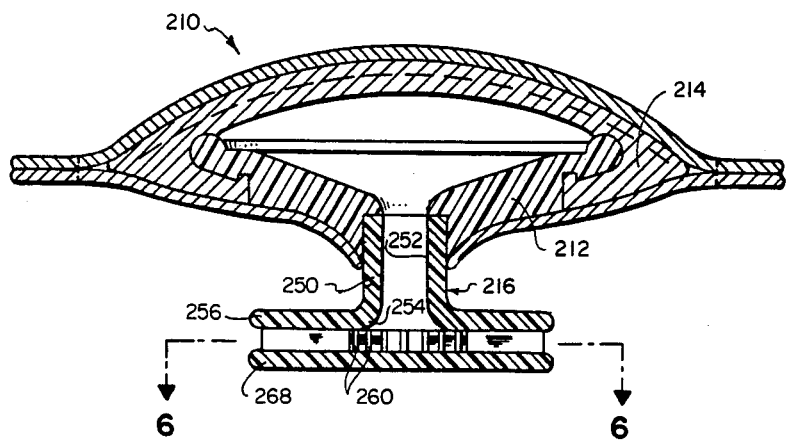
FIG. 5 is a vertical cross-sectional view of a third preferred embodiment of the present invention.
Figure 6:
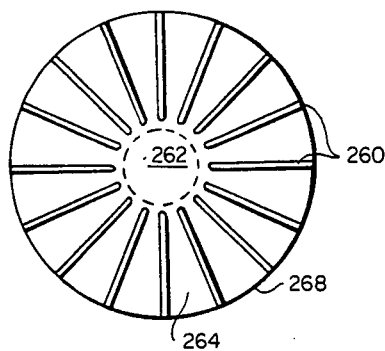
FIG. 6 is a horizontal, cross-sectional view taken along lines 6—6 of FIG. 5.
Figure 7:
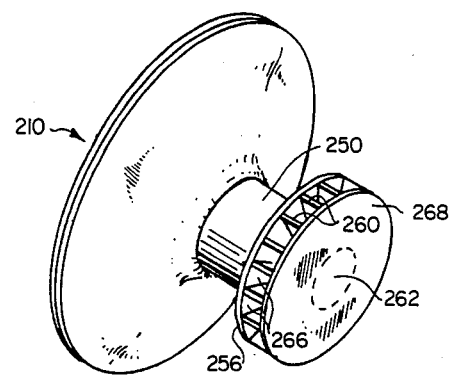
FIG. 7 is a bottom perspective view of the embodiment depicted in FIG. 5.

FIG. 4 depicts a second embodiment of the peritoneal catheter 110 of this invention. As with the previous embodiment, this embodiment also includes a body 112, a cap 114, and a stem 116. The body 112 and cap 14 of this embodiment are in all respects identical to those described in connection with the first embodiment. Similarly, stem 116 is also configured as a hollow, tubular column 150 having two parallel, diametrally enlarged flanges 156 and 158 adjacent the distal end 154 thereof. However, in this embodiment, flange 156 and flange 158 are substantially the same size.

The second embodiment is implanted in a patient in a similar manner as the first embodiment, with flange 156 being secured in place against peritoneal membrane 94 inside peritoneal cavity 96 (see FIG. 1). Should tissue growth or body cell accumulation commence around flange 156, flange 158 acts as a restraining member to inhibit the cells from growing over and obstructing distal end 154.

It will also be appreciated that, while only one opening in distal ends 54 and 154 is illustrated in FIGS. 2-4, both the first and second embodiments of the present invention could have several such openings. Such a configuration would additionally serve to minimize the possibility of catheter obstruction.

FIGS. 5-8 depict a third embodiment of the peritoneal catheter 210 of this invention. The third embodiment also comprises a body 212, a cap 214, and a stem 216. Like the second embodiment, the third embodiment differs from the first embodiment only in the construction and configuration of stem 216. In the third embodiment, tubular column 250 has a diametrally enlarged flange 256 at the distal end 254 thereof. Attached to flange 256 is a generally circular disc 268 having a plurality of radial spacing members 260. As shown best in FIG. 6, disc 268 has a frangible circular area 262 at its center; and each radial spacing member 260 is a narrow strip which is secured along a radius of disc 268 and extends from frangible area 262 to the outer edge of disc 268.

Importantly, frangible area 262 has a diameter which is approximately equal to that of lumen 252. Thus, radial support members 260, together with flange 256 and disc 268, form a plurality of fluid communicating channels 264, which may communicate fluid into the peritoneal cavity through a plurality of openings 266 (see FIG. 7) around the circumference of flange 256.

The third embodiment of catheter 210 is implanted in a patient in the same manner as the first and second embodiments. Should body cells thereafter begin to accumulate near flange 256 of peritoneal catheter 210, it is unlikely that all openings 266 will become occluded so as to prevent fluid flow. Thus, this embodiment of peritoneal catheter 210 also minimizes the possibility of peritoneal injection catheter obstruction.

Figure 8:
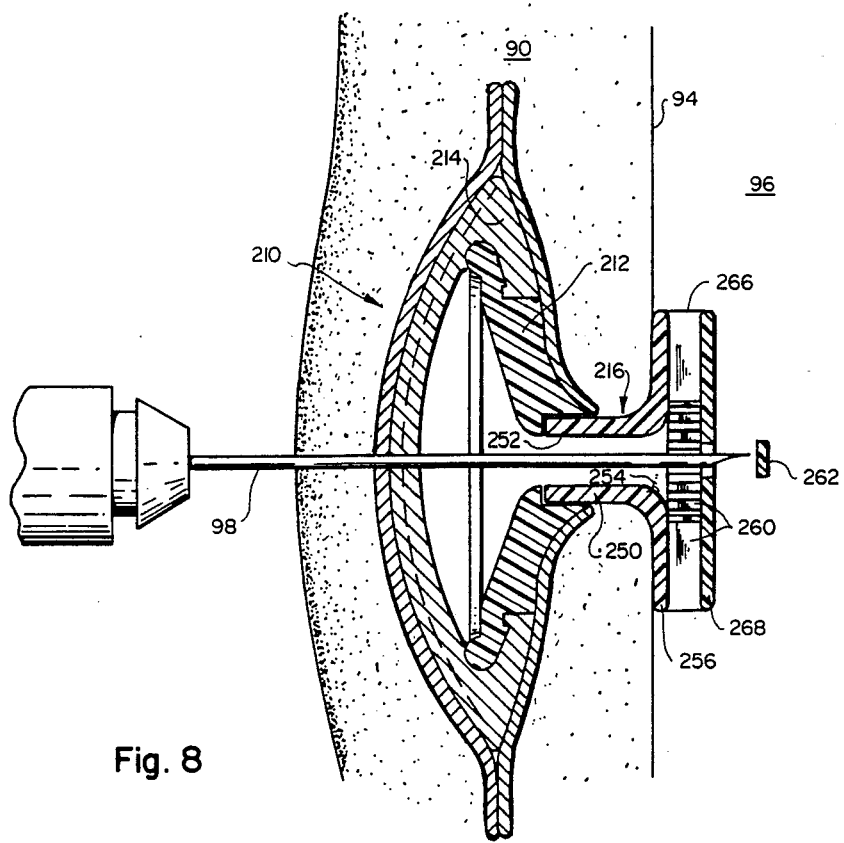
FIG. 8 is a cross-sectional, schematic illustration of the embodiment of FIG. 5 implanted in an abdominal wall and which is shown in cooperation with a trocar which is being used to break out a frangible portion of the base of the catheter.

Referring now more particularly to FIG. 8, the third embodiment of the peritoneal catheter 210 of this invention is shown implanted in abdominal wall 90. A trocar 98 is shown inserted through cap 214 into peritoneal catheter 210 so as to extend down lumen 252 in order to break out frangible area 262. Thus, in the unlikely event that all openings 266 do become obstructed, frangible circular area 262 provides an emergency "bail-out" which serves two primary functions. First, as shown in FIG. 8, frangible circular area 262 provides a means whereby trocar 98 may be pushed into peritoneal cavity 96 in order to push the obstruction away from openings 266 of peritoneal catheter 210. By using trocar 98 in this manner, it may be possible to dislodge an obstructing body from peritoneal catheter 210 so as to free openings 266 for fluid flow. Second, frangible circular area 262 provides an alternate opening into peritoneal catheter 96 in the event that all openings 266 become permanently obstructed.

It will be appreciated that the above-described configurations for the peritoneal catheter of the present invention will significantly reduce the likelihood that the catheter will become obstructed during use. In addition, however, a portion of the catheter may advantageously be formed of or covered with a suitable cellulicidal material (that is, a material which kills growing cells).

Suitable cellulicidal materials include, for example, silver, platinum-silver, and copper. Each of these materials has a toxic effect on growing cells, while remaining safe for internal use. Silver and platinum-silver, for example, are oligodynamic materials, that is, they are effective as sterilizing agents in small quantities. Copper also acts as a sterilizing agent by leaching a toxic substance into surrounding fluids. However, it has been found that the quantity of the toxin leached by the copper is no greater than the quantity of toxins which are naturally present in mother's milk. Thus, the use of copper within the body is considered to be safe.

In order to further deter tissue or bacteria growth and accumulation, therefore, a portion of the catheter may be formed of or coated with one of these cellulicidal materials. For example, one of these materials could be used to form the distal end of the hollow stem of the catheter. Alternatively, a plurality of concentric rings could be provided on any or all of the diametrally enlarged flanges of the catheter, particularly on those flanges which are immediately adjacent the peritoneal opening of the catheter.

These materials may also be advantageously used within the peritoneal catheter of the present invention in order to inhibit the growth of bacteria within the catheter. Thus, for example, the interior of the peritoneal catheter could be coated with silver by sputtering the device with silver paint prior to assembly. Alternatively, silver could be incorporated into the various plastic materials used in forming the catheter. In such case, the silver could either be in the form of a fine powder or as a silver mesh or screen.

In light of the foregoing, it can be appreciated that the novel peritoneal injection catheter and the embodiments described above significantly minimize the possibility of peritoneal catheter obstruction. Both the geometrical configuration and the use of cellulicidal materials on this improved peritoneal injection catheter minimize the possibility of obstruction due to omentum overgrowth, tissue ingrowth, and/or other body cell accumulation. Further, by providing for a cellulicidal material within the catheter, this invention also minimizes the likelihood that bacteria will grow and accumulate within the subcutaneous reservoir of the peritoneal catheter. Significantly, this invention comprises a method for minimizing catheter obstruction while maintaining the structural integrity of the peritoneal catheter. Thus, it will be appreciated that the peritoneal catheter of this invention is an improved implantable subcutaneous peritoneal injection catheter which may be used by a single patient over a relatively long period of time without interruption or malfunction.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A subcutaneously implantable injection conduit for injecting a drug into a peritoneal cavity, comprising:
   a hollow receptacle for receiving the drug, the hollow receptacle having a penetrable portion;
   a hollow stem having a proximal end and a distal end, the proximal end of the stem being attached to the receptacle such that the stem forms a passageway extending from the chamber;
   a first substantially diametrally enlarged flange attached to the stem such that, when the conduit is implanted under a layer of skin adjacent the peritoneal cavity and the first flange is secured adjacent the parietal peritoneal membrane, the distal end of the hollow stem is positioned within the peritoneal catheter; and
   structural means for inhibiting cell growth which would inhibit flow through the hollow stem comprising a second substantially rigid, diametrically enlarged flange attached to the stem within the peritoneal cavity.

2. A subcutaneously implantable injection conduit as defined in claim 1 wherein the structural means for inhibiting cell growth comprises a second diametrally enlarged flange, said second flange being attached to the stem in spaced relationship with the first flange.

3. A subcutaneously implantable injection conduit as defined in claim 2 wherein the second flange is substantially parallel to the first flange.

4. A subcutaneously implantable injection conduit as defined in claim 2 wherein the second flange is attached adjacent the distal end of the hollow stem.

5. A subcutaneously implantable injection conduit as defined in claim 2 wherein the second flange is diametrally smaller than the first flange.

6. A subcutaneously implantable injection conduit as defined in claim 2 wherein the second flange is substantially the same size as the first flange.

7. A subcutaneously implantable injection conduit as defined in claim 1 wherein the structural means for inhibiting cell growth comprises:
   a tube having a proximal end and a distal end, said tube being secured within the hollow stem such that the proximal end of the tube lies within the passageway and the distal end of the tube protrudes from the distal end of the hollow stem; and
   a second diametrally enlarged flange attached adjacent the distal end of the tube so as to be in spaced relationship with the first flange.

8. A subcutaneously implantable injection conduit as defined in claim 7 wherein the second flange is diametrally smaller than the first flange.

9. A subcutaneously implantable injection conduit as defined in claim 1 wherein the structural means for inhibiting cell growth comprises a diametrally enlarged solid disc having spacing members attached to one side thereof, said spacing members also being attached to the first flange such that the first flange and the disc form a circumferential opening which communicates with the passageway.

10. A subcutaneously implantable injection conduit as defined in claim 9 wherein the spacing members are configurated as narrow strips, each of which is attached along a radius of the disc.

11. A subcutaneously implantable injection conduit as defined in claim 9 wherein a portion of the disc which is in direct line with the passageway is frangible, such that said frangible portion may be broken out of the disc by means of a rigid instrument inserted through the passageway.

12. A subcutaneously implantable injection conduit as defined in claim 11 wherein the frangible portion is substantially circular in shape.

13. A subcutaneously implantable injection conduit for injecting a drug into a peritoneal cavity, comprising:
   a hollow receptacle for receiving the drug, the hollow receptacle having a penetrable portion;
   a hollow stem having a proximal end and a distal end, the proximal end of the stem being attached to the receptacle such that the stem forms a passageway extending from the chamber;
   a first diametrally enlarged flange attached to the stem such that, when the conduit is implanted under a layer of skin adjacent the peritoneal cavity and the first flange is secured adjacent the parietal peritoneal membrane, the distal end of the hollow stem is positioned within the peritoneal cavity; and
   a cellulicidal material covering at least a portion of the injection conduit for inhibiting cell growth which would inhibit flow through the hollow stem.

14. A subcutaneously implantable injection conduit as defined in claim 13 wherein the cellulicidal material is silver.

15. A subcutaneously implantable injection conduit as defined in claim 13 wherein the cellulicidal material is platinum-silver.

16. A subcutaneously implantable injection conduit as defined in claim 13 wherein the cellulicidal material is copper.

17. A subcutaneously implantable injection conduit as defined in claim 13 wherein the conduit is formed of a plastic material and wherein the cellulicidal material is dispersed within the plastic.

18. A subcutaneously implantable injection conduit as defined in claim 17 wherein the cellulicidal material is silver.

19. A subcutaneously implantable injection conduit as defined in claim 1 further comprising a cellulicidal material for suppressing cell growth covering at least a part of the hollow receptacle and the hollow stem.

20. A subcutaneously implantable injection conduit as defined in claim 19 wherein the cellulicidal material covers at least a portion of the interior surface of the hollow receptacle and the hollow stem.

21. A subcutaneously implantable injection conduit as defined in claim 20 wherein the cellulicidal material is silver.

22. A subcutaneously implantable injection conduit as defined in claim 20 wherein the cellulicidal material is platinum-silver.

23. A subcutaneously implantable injection conduit as defined in claim 20 wherein the cellulicidal material is copper.

24. A subcutaneously implantable injection conduit as defined in claim 19 wherein the conduit is formed of a plastic material and wherein the cellulicidal material is dispersed within the plastic.

25. A subcutaneously implantable injection conduit as defined in claim 24 wherein the cellulicidal material is silver.

26. A subcutaneously implantable injection conduit for injecting a drug into a peritoneal cavity, comprising:
a hollow receptacle for receiving the drug, the hollow receptacle having a penetrable portion;
a hollow stem having a proximal end and a distal end, the proximal end of the stem being attached to the receptacle such that the stem forms a passageway extending from the chamber;
a first diametrally enlarged flange attached to the stem such that, when the conduit is implanted under a layer of skin adjacent the peritoneal cavity and the first flange is secured adjacent the parietal peritoneal membrane, the distal end of the hollow stem is directed toward the mesenteric peritoneal membrane; and
a cellulicidal material for inhibiting cell growth covering at least a part of the hollow receptacle and the hollow stem.

27. A subcutaneously implantable injection conduit as defined in claim 26 wherein the cellulicidal material covers at least a portion of the interior surface of the hollow receptacle and the hollow stem.

28. A subcutaneously implantable injection conduit as defined in claim 27 wherein the cellulicidal material is silver.

29. A subcutaneously implantable injection conduit as defined in claim 27 wherein the cellulicidal material is platinum-silver.

30. A subcutaneously implantable injection conduit as defined in claim 27 wherein the cellulicidal material is copper.

31. A subcutaneously implantable injection conduit as defined in claim 26 wherein the conduit is formed of a plastic material and wherein the cellulicidal material is dispersed within the plastic.

32. A subcutaneously implantable injection conduit as defined in claim 31 wherein the cellulicidal material is silver.

33. A subcutaneously implantable injection conduit for injecting a drug into a peritoneal cavity, comprising:
an injection receiver having a diametrally enlarged, convergent receiving surface and an opening in the receiving surface;
a diametrally enlarged, penetrable cover across the receiving surface in spaced relationship therewith, the cover forming a receiving reservoir in combination with the receiving surface;
a hollow stem having a proximal end and a distal end, the proximal end of the stem being attached to the injection receiver such that the stem forms a passageway extending from the opening in the receiving surface, the stem having a length sufficient that the stem penetrates the parietal peritoneal membrane and extends into the peritoneal cavity;
a first substantially rigid diametrally enlarged flange attached to the stem such that, when the conduit is implanted under a layer of skin adjacent the peritoneal cavity and the first flange is secured adjacent the parietal peritoneal membrane, the distal end of the hollow stem is directed toward the mesenteric peritoneal membrane; and
structural means adjacent the distal end of the hollow stem for preventing obstruction of the passageway comprising a second substantially rigid, diametrically enlarged flange attached to the stem within the peritoneal cavity.

34. A subcutaneously implantable injection conduit as defined in claim 33 wherein the obstruction preventing means comprises a second diametrally enlarged flange, said second flange being attached to the stem in spaced relationship with the first flange.

35. A subcutaneously implantable injection conduit as defined in claim 34 wherein the second flange is substantially parallel to the first flange.

36. A subcutaneously implantable injection conduit as defined in claim 35 wherein the second flange is attached adjacent the distal end of the hollow stem.

37. A subcutaneously implantable injection conduit as defined in claim 36 wherein at least a portion of the injection conduit is formed of a cellulicidal material.

38. A subcutaneously implantable injection conduit as defined in claim 37 wherein the cellulicidal material is silver.

39. A subcutaneously implantable injection conduit as defined in claim 37 wherein the cellulicidal material is platinum-silver.

40. A subcutaneously implantable injection conduit as defined in claim 37 wherein the cellulicidal material is copper.

41. A subcutaneously implantable injection conduit as defined in claim 36 wherein the conduit is formed of a plastic material which has a cellulicidal material dispersed therein.

42. A subcutaneously implantable injection conduit as defined in claim 41 wherein the cellulicidal material is silver.

43. A subcutaneously implantable injection conduit as defined in claim 33 wherein the obstruction preventing means comprises a diametrally enlarged disc having spacing members attached to one side thereof, said spacing members also being attached to the first flange such that the first flange and the disc form a circumferential opening which communicates with the passageway.

44. A subcutaneously implantable injection conduit as defined in claim 43 wherein the spacing members are configured as narrow strips, each of which is attached along a radius of the disc.

45. A subcutaneously implantable injection conduit as defined in claim 44 wherein a portion of the disc which is in direct line with the passageway is frangible, such that said frangible portion may be broken out of the disc by means of a rigid instrument inserted through the passageway.

46. A subcutaneously implantable injection conduit as defined in claim 45 wherein the frangible portion is substantially circular in shape.

47. A subcutaneously implantable injection conduit as defined in claim 46 wherein at least a portion of the injection conduit is formed of a cellulicidal material.

48. A subcutaneously implantable injection conduit as defined in claim 47 wherein the cellulicidal material is silver.

49. A subcutaneously implantable injection conduit as defined in claim 47 wherein the cellulicidal material is platinum-silver.

50. A subcutaneously implantable injection conduit as defined in claim 47 wherein the cellulicidal material is copper.

51. A subcutaneously implantable injection conduit as defined in claim 46 wherein the conduit is formed of a plastic material which has a cellulicidal material dispersed therein.

52. A subcutaneously implantable injection conduit as defined in claim 51 wherein the cellulicidal material is silver.

53. A method for minimizing peritoneal injection catheter obstruction, the method comprising the steps of:
   obtaining an injection conduit, comprising:
      a shallow vessel with an open top;
      a penetrable membrane covering the open top of the vessel;
      a hollow stem having a proximal end and a distal end, the proximal end of the stem being attached to the vessel such that the stem forms a passagweway extending from the vessel; and
      a diametrally enlarged flange attached to the stem such that, when the conduit is implanted underneath a layer of skin adjacent the peritoneal cavity and the flange is secured adjacent the parietal peritoneal membrane, the distal end of the hollow stem is directed toward the mesenteric peritoneal membrane;
   implanting the injection conduit underneath a layer of skin adjacent the peritoneal cavity with the membrane being generally parallel to the skin, the hollow stem penetrating the parietal peritoneal membrane and extending into the peritoneal cavity, the diametrally enlarged flange being secured adjacent the parietal peritoneal membrane, the distal end of the hollow stem being directed toward the mesenteric peritoneal membrane, and the passageway communicating between the vessel and the peritoneal cavity;
   penetrating the layer of skin and the membrane with a rigid instrument such that the rigid instrument moves down the passagweway; and
   pushing the rigid instrument through the distal end of the hollow stem so as to force obstructing objects away from the catheter.

54. A method for minimizing peritoneal injection catheter obstruction as defined in claim 53 wherein a portion of the injection conduit adjacent the distal end of the hollow stem is frangible and wherein the instrument pushing step is preceded by an instrument forcing step which comprises:
   forcing the rigid instrument against the frangible portion of the injection conduit so as to break said frangible portion.

55. A method for minimizing peritoneal injection catheter obstruction as defined in claim 54 wherein the rigid instrument is a trocar.

56. A method for minimizing peritoneal injection catheter obstruction as defined in claim 53 wherein the injection conduit further comprises:
   a diametrally enlarged disc, a portion of said disc being frangible and said disc having spacing members attached to one side thereof, said spacing members also being attached to the first flange such that the frangible portion is in direct line with the passageway and such that the first flange and the disc form a circumferential opening which communicates with the passageway;
   and wherein the instrument pushing step is preceded by an instrument forcing step which comprises:
   forcing the rigid instrument against the frangible portion of the disc so as to break said frangible portion.

* * * * *

UNITED STATES PATENT AND TRADEMARK OFFICE
CERTIFICATE OF CORRECTION

PATENT NO.    : 4,559,033
DATED         : December 17, 1985
INVENTOR(S)   : ROBERT L. STEPHEN et al.

It is certified that error appears in the above-identified patent and that said Letters Patent is hereby corrected as shown below:

Column 3, line 43, "epineephrine" should be --epinephrine--
Column 5, line 10, "gold tee" should be --golf tee--
Column 9, line 9, "with the catheter" should be --within the catheter--
Column 9, line 42, "with peritoneal" should be --from peritoneal--
Column 11, line 12, "surfac" should be --surface--
Column 11, line 37, "cap 14" should be --cap 114--
Column 13, line 52, after "substantially" insert --rigid--
Column 17, lines 46-47, "passagweway" should be --passageway--

Signed and Sealed this

*Eleventh* Day of *March 1986*

[SEAL]

*Attest:*

DONALD J. QUIGG

*Attesting Officer*    *Commissioner of Patents and Trademarks*